United States Patent
Kalgutkar et al.

(10) Patent No.: US 9,351,908 B2
(45) Date of Patent: May 31, 2016

(54) ORTHODONTIC COMPOSITION WITH POLYMERIC FILLERS

(71) Applicant: 3M INNOVATIVE PROPERTIES COMPANY, St. Paul, MN (US)

(72) Inventors: Rajdeep S. Kalgutkar, Woodbury, MN (US); David T. Amos, St. Paul, MN (US); Taun L. McKenzie, Hugo, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 14/466,626

(22) Filed: Aug. 22, 2014

(65) Prior Publication Data

US 2014/0363777 A1    Dec. 11, 2014

Related U.S. Application Data

(63) Continuation of application No. 12/671,522, filed as application No. PCT/US2008/076959 on Sep. 19, 2008, now abandoned.

(60) Provisional application No. 60/976,501, filed on Oct. 1, 2007.

(51) Int. Cl.
*A61K 6/083* (2006.01)
*A61K 6/00* (2006.01)
*A61C 7/16* (2006.01)

(52) U.S. Cl.
CPC .............. *A61K 6/0023* (2013.01); *A61C 7/16* (2013.01); *A61K 6/0008* (2013.01); *A61K 6/0052* (2013.01)

(58) Field of Classification Search
USPC ....................................... 523/118; 433/228.1
See application file for complete search history.

(56) References Cited

U.S. PATENT DOCUMENTS

| | | | |
|---|---|---|---|
| 3,018,262 A | 1/1962 | Schroeder |
| 3,625,916 A | 12/1971 | Newman |
| 3,629,187 A | 12/1971 | Waller et al. |
| 3,923,740 A | 12/1975 | Schmitt et al. |
| 4,259,075 A | 3/1981 | Yamauchi et al. |
| 4,277,536 A | 7/1981 | Podszun et al. |
| 4,298,738 A | 11/1981 | Lechtken et al. |
| 4,324,744 A | 4/1982 | Lechtken et al. |
| 4,356,296 A | 10/1982 | Griffith et al. |
| 4,385,109 A | 5/1983 | Lechtken et al. |
| 4,435,160 A | 3/1984 | Randklev |
| 4,479,782 A | 10/1984 | Orlowski et al. |
| 4,499,251 A | 2/1985 | Omura et al. |
| 4,503,169 A | 3/1985 | Randklev |
| 4,537,940 A | 8/1985 | Omura et al. |
| 4,539,382 A | 9/1985 | Omura et al. |
| 4,642,126 A | 2/1987 | Zador et al. |
| 4,648,843 A | 3/1987 | Mitra |
| 4,652,274 A | 3/1987 | Boettcher et al. |
| 4,665,217 A | 5/1987 | Reiners et al. |
| 4,695,251 A | 9/1987 | Randklev |
| 4,710,523 A | 12/1987 | Lechtken et al. |
| 4,737,593 A | 4/1988 | Ellrich et al. |
| 4,752,338 A | 6/1988 | Reiners et al. |
| 4,872,936 A | 10/1989 | Engelbrecht |
| 4,906,185 A | 3/1990 | Randklev |
| 4,937,144 A | 6/1990 | Podszun |
| 4,978,007 A | 12/1990 | Jacobs et al. |
| 5,015,180 A | 5/1991 | Randklev |
| 5,026,902 A | 6/1991 | Fock et al. |
| 5,037,861 A | 8/1991 | Crivello et al. |
| 5,063,257 A | 11/1991 | Akahane et al. |
| 5,076,844 A | 12/1991 | Fock et al. |
| 5,112,880 A | 5/1992 | Tsunekawa et al. |
| 5,130,347 A | 7/1992 | Mitra |
| 5,154,762 A | 10/1992 | Mitra et al. |
| 5,227,413 A | 7/1993 | Mitra |
| 5,238,736 A | 8/1993 | Tseng et al. |
| 5,328,363 A | 7/1994 | Chester et al. |
| 5,367,002 A | 11/1994 | Huang et al. |
| 5,501,727 A | 3/1996 | Wang et al. |

(Continued)

FOREIGN PATENT DOCUMENTS

EP    0037677 A2    10/1981
EP    0173567        3/1986

(Continued)

OTHER PUBLICATIONS

Gwinnett and Gorelick, Microscopic Evaluation of Enamel After Debonding: Clinical Application; Am. J. Orthod., vol. 71, No. 6, pp. 651-665 (Jun. 1977).

Jonke et al.; Heat Generated by Residual Adhesive Removal After Debonding of Brackets; World Journal of Orthodontics, vol. 7, p. 357 (2006).

Mathis et al., Properties of a Glass-Ionomer/Resin-Composite Hybrid Material, Dental Materials/Sep. 1989, pp. 355-358.

Okina, Fundamental Study of Experimental Visible Light-Activated Direct Bonding Adhesives with Organic Filler, J. Fukuoka Dent. Coll. 24(2) pp. 199-215, 1997.

(Continued)

*Primary Examiner* — Tae H Yoon
(74) *Attorney, Agent, or Firm* — Philip P. Soo; Kevin W. Weber

(57) ABSTRACT

Orthodontic adhesives are claimed which use polymeric filler particles with defined particle size characteristics. The particle size characteristics are controlled such that these adhesives provide comparable mechanical retention and cohesive strength of conventional orthodontic adhesives when used to bond orthodontic appliances to teeth. Because polymeric fillers are generally softer than inorganic fillers, these adhesives are easier to remove from the tooth than conventional adhesives after debonding an orthodontic appliance. Embodiments of the invention include both self-curing and two-part adhesives, packaged adhesive-coated orthodontic appliances, and methods for removing a cured adhesive from a tooth surface.

20 Claims, 1 Drawing Sheet

(56) References Cited

U.S. PATENT DOCUMENTS

| | | | |
|---|---|---|---|
| 5,520,725 A | 5/1996 | Kato et al. |
| 5,530,038 A | 6/1996 | Yamamoto et al. |
| 5,545,676 A | 8/1996 | Palazzotto et al. |
| 5,856,373 A | 1/1999 | Kaisaki et al. |
| 5,859,089 A | 1/1999 | Qian |
| 5,871,360 A | 2/1999 | Kato |
| 5,925,715 A | 7/1999 | Mitra |
| 5,962,550 A | 10/1999 | Akahane et al. |
| 5,965,632 A | 10/1999 | Orlowski et al. |
| 6,008,157 A | 12/1999 | Takeuchi |
| 6,013,694 A | 1/2000 | Jia et al. |
| 6,015,597 A | 1/2000 | David |
| 6,030,606 A | 2/2000 | Holmes |
| 6,045,913 A | 4/2000 | Castle |
| 6,084,004 A | 7/2000 | Weinmann et al. |
| 6,090,867 A | 7/2000 | Starling, Jr. et al. |
| 6,183,249 B1 | 2/2001 | Brennan et al. |
| 6,187,833 B1 | 2/2001 | Oxman et al. |
| 6,187,836 B1 | 2/2001 | Oxman et al. |
| 6,197,120 B1 | 3/2001 | David |
| 6,245,828 B1 | 6/2001 | Weinmann et al. |
| 6,251,963 B1 | 6/2001 | Kohler et al. |
| 6,331,080 B1 | 12/2001 | Cole et al. |
| 6,387,981 B1 | 5/2002 | Zhang et al. |
| 6,444,725 B1 | 9/2002 | Trom et al. |
| 6,458,868 B1 | 10/2002 | Okada et al. |
| 6,528,555 B1 | 3/2003 | Nikutowski et al. |
| 6,566,413 B1 | 5/2003 | Weinmann et al. |
| 6,572,693 B1 | 6/2003 | Wu et al. |
| 6,624,236 B1 | 9/2003 | Bissinger et al. |
| 6,669,927 B2 | 12/2003 | Trom et al. |
| 6,670,436 B2 | 12/2003 | Burgath et al. |
| 6,759,449 B2 | 7/2004 | Kimura |
| 6,765,036 B2 | 7/2004 | Dede et al. |
| 6,765,038 B2 | 7/2004 | Mitra |
| 6,779,656 B2 | 8/2004 | Klettke et al. |
| 6,799,969 B2 | 10/2004 | Sun et al. |
| 6,852,795 B2 | 2/2005 | Bissinger et al. |
| 6,852,822 B1 | 2/2005 | Bissigner et al. |
| 6,878,419 B2 | 4/2005 | David et al. |
| 6,960,079 B2 | 11/2005 | Brennan et al. |
| 6,982,288 B2 | 1/2006 | Mitra et al. |
| 7,090,721 B2 | 8/2006 | Craig et al. |
| 7,090,722 B2 | 8/2006 | Budd et al. |
| 7,137,812 B2 | 11/2006 | Cleary et al. |
| 7,156,911 B2 | 1/2007 | Kangas et al. |
| 7,173,074 B2 | 2/2007 | Mitra et al. |
| 7,175,433 B2 | 2/2007 | Sun et al. |
| 7,214,726 B2 | 5/2007 | Qian |
| 7,262,228 B2 | 8/2007 | Oxman |
| 7,632,098 B2 | 12/2009 | Falsafi |
| 7,649,029 B2 | 1/2010 | Kolb |
| 7,741,005 B2 | 6/2010 | Yanaka |
| 8,722,760 B2 | 5/2014 | Luchterhandt |
| 2003/0196914 A1 | 10/2003 | Tzou et al. |
| 2003/0198913 A1 | 10/2003 | Cinader, Jr. |
| 2004/0039079 A1* | 2/2004 | Qian ............... A61K 6/0023 523/115 |
| 2004/0151691 A1 | 8/2004 | Oxman et al. |
| 2004/0206932 A1 | 10/2004 | Abuelyaman et al. |
| 2005/0133384 A1 | 6/2005 | Cinader et al. |
| 2008/0096150 A1* | 4/2008 | Cinader ............... A61C 7/14 433/9 |

FOREIGN PATENT DOCUMENTS

| | | |
|---|---|---|
| EP | 0201031 | 11/1986 |
| EP | 0201778 | 11/1986 |
| EP | 0373384 | 6/1990 |
| EP | 712622 | 5/1996 |
| EP | 1051961 | 11/2000 |
| EP | 1249221 | 10/2002 |
| EP | 1393705 | 3/2004 |
| EP | 0897710 | 11/2004 |
| FR | 2363613 | 3/1978 |
| GB | 1267448 | 3/1972 |
| GB | 2006792 A | 5/1979 |
| JP | 02-252775 | 10/1990 |
| JP | H05-085912 | 4/1993 |
| JP | 2007-320929 A | 12/2007 |
| WO | WO 00/38619 | 7/2000 |
| WO | WO 00/42092 | 7/2000 |
| WO | WO 00/69393 | 11/2000 |
| WO | WO 01/07444 | 2/2001 |
| WO | WO 01/30305 | 5/2001 |
| WO | WO 01/30306 | 5/2001 |
| WO | WO 01/30307 | 5/2001 |
| WO | WO 01/92271 | 6/2001 |
| WO | WO 01/51540 | 7/2001 |
| WO | WO 03/063804 | 8/2003 |
| WO | WO 2010/039395 | 4/2010 |

OTHER PUBLICATIONS

Zach et al.; Endodontics: Pulp Response to Externally Applied Heat; Oral Surg. Oral Med. Oral Pathol. (Apr. 1965) vol. 19, pp. 515-530.
Retief and Denys, Finishing of Enamel Surfaces After Debonding of Orthodontic Attachments, Angle Orthodontist, vol. 49, No. 1, pp. 1-10 (Jan. 1979).
Handbook of Epoxy Resins, by Lee and Neville, McGraw-Hill Book Co., New York (1967); Ch. 14-Fillers for Epoxy Resins, pp. 14-1 to 14-50.
International Search Report for PCT/US2008/076959, prepared by the European Patent Office, Netherlands, mailed Jul. 12, 2010, 4 pgs.

* cited by examiner

ORTHODONTIC COMPOSITION WITH POLYMERIC FILLERS

1. RELATED APPLICATIONS

This patent application is a continuation application that claims the benefit of and priority to U.S. patent application Ser. No. 12/671,522, filed Sep. 19, 2008, now abandoned which claims the benefit of and priority to International PCT Application PCT/US2008/076959, filed Sep. 19, 2008, which claims the benefit of and priority to provisional application 60/976501, filed Oct. 1, 2007, the disclosure of which is incorporated by reference in its/their entirety herein.

BACKGROUND OF THE INVENTION

1. Field of the Invention

The present invention broadly pertains to an orthodontic composition. More particularly, this invention pertains to an orthodontic adhesive that contains polymeric fillers.

2. Description of the Related Art

Orthodontic therapy is a specialized type of treatment within the field of dentistry associated with the supervision, guidance and correction of malpositioned teeth into proper locations. Orthodontic treatment can be useful in correcting defects in a patient's bite (also called occlusion) along with promoting better hygiene and improving the overall aesthetics of the teeth.

Orthodontic treatment often involves the use of tiny slotted appliances known as brackets, which are generally affixed to the patient's anterior, cuspid, and bicuspid teeth. After the brackets have been placed on the teeth, an archwire is received into the slot of each bracket and acts as a track to guide the movement of respective teeth to orthodontically correct positions. End sections of the archwire are typically received in appliances known as buccal tubes that are affixed to the patient's molar teeth. The combination of brackets, archwires, and buccal tubes is commonly referred to as an orthodontic brace, or "braces".

It is common practice for orthodontists to use adhesives to bond orthodontic appliances to the surface of the tooth. This may be accomplished using a direct bonding method, which involves applying an adhesive to the appliance base, mounting the appliance to a tooth, removing any excess adhesive flash that has been extruded out along the base of the appliance, and finally hardening the adhesive. Alternatively, an indirect method may be used, in which appliances are first adhesively bonded to a replica of the patient's teeth (commonly made from plaster or orthodontic stone) and a resilient transfer tray formed over the appliances and the replica. The transfer tray is then used to carefully detach the appliances from the replica and re-bond the appliances simultaneously to the teeth of a patient, again using an appropriate adhesive. A variety of adhesives are available to the clinician for bonding appliances to tooth surfaces, and many offer excellent bond strengths. High bond strengths are desirable for maintaining adhesion of the appliance to the tooth surface over the duration of the treatment process, which can typically be two years or more.

At the conclusion of orthodontic treatment, all of the appliances are debonded from the teeth of the patient. There are also situations, however, in which appliances are removed from teeth prior to the conclusion of treatment. For example, the orthodontist may remove and re-position just one or two appliances in the middle of treatment to achieve a particular treatment goal. It is also possible that one or more appliances may become accidentally debonded when the patient bites down on a hard food substance.

In each of the above situations, some amount of residual adhesive is usually left on the tooth surface where the appliance was debonded, and this adhesive should be meticulously removed by the dental professional. Conventional orthodontic adhesives are highly crosslinked and usually contain hard inorganic fillers, such as silica. Moreover, these fillers are often present in amounts exceeding 50 weight percent of the adhesive in order to achieve high strength and acceptable adhesive handling properties. Once hardened, these materials tend to be difficult and time-consuming to remove from the patient's teeth. Presently, the removal process often involves the use of a hand tool with a rotating tip such as a fluted tungsten carbide burr operating in the range of 20,000 to 200,000 rpm. Because tungsten carbide is a relatively hard material compared with tooth enamel, there is some risk that the tip will accidentally cause enamel damage, and as a result this removal task is generally carried out by the orthodontist and not delegated to assistants.

Grinding adhesive from the tooth takes a substantial amount of time and it is often cited as one of the most cumbersome procedures, for both orthodontist and patient, of the entire orthodontic treatment. Furthermore, since the orthodontist's time is very valuable relative to an assistant's time, any procedure only carried out by the orthodontist is inefficient from a financial and/or office management standpoint.

There are also other risks associated with using a high speed rotary hand tool on a patient. High rotation speeds cause frictional heating of the enamel surface by the fluted burr. Although this heating can be alleviated using a stream of coolant water, many clinicians avoid using such a coolant because it is often easier to see remnant adhesive on the enamel when the site is dry. Recent studies suggest that the temperature rise in the pulpal chamber caused by grinding using a fluted burr may be as high as 9.5° C. if a 6-fluted carbide burr is used (Jonke et al. *World Journal of Orthodontics*, Vol. 7, p. 357 (2006)). Tooth pulpal damage can occur at these temperatures (Zach et al. *Oral Surg. Oral Med. Oral Pathol.* (1965) Vol. 19, pp. 515-530).

Some references have suggested using lower amounts of filler in an orthodontic adhesive than the amounts typically used, to ease removal of residual adhesive. Some of these concepts are described in Gwinnett and Gorelick, *Am. J. Orthod.*, Vol. 71, No. 6, pp. 651-665 (June 1977), Retief and Denys, "Finishing of Enamel Surfaces After Debonding of Orthodontic Attachments", *Angle Orthodontist*, Vol. 49, No. 1, pp. 1-10 (January 1979), and U.S. Pat. No. 3,629,187 (Waller, et al.). However, removal of residual adhesive containing these fillers still can lead to enamel damage because hardened tools must be used to grind away the residual adhesive. Clearly, any damage to the pulp of the tooth should be avoided if possible.

SUMMARY OF THE INVENTION

There is a need for an improved orthodontic adhesive that offers excellent handling and bond reliability, and also facilitates adhesive removal after the appliances have been debonded from the teeth. The present invention is directed to an orthodontic adhesive which includes polymeric filler particles with defined particle size characteristics. The particle size characteristics are controlled such that these adhesives provide comparable mechanical retention and cohesive strength of conventional orthodontic adhesives when used to bond orthodontic appliances to teeth. However, by virtue of polymeric fillers being softer than most inorganic fillers, these adhesives are generally easier to remove from the tooth surface after debonding of an orthodontic appliance than conventional adhesives.

Preferably, the adhesive is essentially free of all hard inorganic fillers (i.e., with a Mohs hardness of at least 5). Most conventional adhesives contain quartz filler, or derivatives such as silica glass, which display levels of hardness around 7 on the Mohs hardness scale, compared with a Mohs hardness of 5 for enamel. These values compare to a Mohs hardness of 9 for a fluted tungsten carbide burr, which is commonly used to remove conventional residual adhesive from the tooth after an appliance is debonded. By contrast, the polymeric fillers of the present invention display hardness levels less than 5 on the Mohs hardness scale. Because these materials are comparatively soft, residual adhesive can be removed more thoroughly and easily using a prophy paste or finishing tool such as a scalar or dental finishing disk. By avoiding the need to use a high speed carbide burr for adhesive clean up, the process is shorter and more comfortable to the patient, less heat is generated at the tooth surface and the risk of enamel damage is significantly reduced. Together, the ease of adhesive cleanup, improved patient comfort, and reduced risk of tooth damage provide benefits to both the orthodontist and patient.

In one aspect, the present invention provides an orthodontic adhesive including a hardenable component, a hardener, and a polymeric filler. The polymeric filler has a particle size median in a range from 6 to 18 micrometers. In certain embodiments, the polymeric filler has a size distribution that is characterized by a d50/d25 particle size ratio, as described below, of less than 2.5. Fillers may be prepared using emulsion polymerization or suspension polymerization, and may be crosslinked. In other embodiments, compositions further include other polymeric fillers or an inorganic filler. In certain embodiments, the overall filler loading is present in a range from 55 to 65 weight percent, based on the overall weight of the adhesive. Optionally, the composition includes an inorganic filler that releases fluoride. If the inorganic filler has a Mohs hardness of at least 5, it is preferable that the inorganic component is present in a range from 0 to 5 weight percent, based on the overall weight of the adhesive.

In another aspect, the present invention provides a two-part orthodontic adhesive that includes a first adhesive composition containing an oxidizing agent and a second adhesive composition containing a reducing agent, wherein at least one of the first adhesive composition and the second adhesive composition comprises a polymeric filler that has a particle size median in a range from 6 micrometers to 18 micrometers, and further wherein the orthodontic adhesive is hardened by contacting the first adhesive composition and second adhesive composition with each other.

In another aspect, the present invention provides a packaged article that includes an orthodontic appliance having a base for bonding the appliance to a tooth and an adhesive on the base of the appliance. The adhesive includes a hardenable component, a hardener, and a polymeric filler that has a median particle size in a range from 6 micrometers to 18 micrometers. A container at least partially surrounds the orthodontic appliance having adhesive on the base thereof.

In another aspect, the present invention provides a method for removing cured orthodontic adhesive from a tooth. In one embodiment, the method includes providing a tooth surface having a cured orthodontic adhesive on at least a portion of the surface thereon, the adhesive comprising a hardenable component, a hardener, and a polymeric filler with a particle size median in a range from 6 micrometers to 18 micrometers, and applying an abrasive to the tooth surface to remove the adhesive from the tooth. The abrasive has a Mohs hardness that is less than 5 and is optionally a finishing disk or a prophy powder.

BRIEF DESCRIPTION OF THE DRAWINGS

The present invention will be described with respect to the attached Figures, in which.

DETAILED DESCRIPTION OF THE PREFERRED EMBODIMENTS

The exemplary orthodontic adhesives described herein constitute composite materials each comprising at least one polymeric or hybrid filler, a hardenable component, a hardener, and optionally, an additive that provides a secondary function such as a color change feature. Hardenable and hardened adhesives as described herein can be used for a variety of dental and orthodontic applications that use a material capable of adhering (e.g., bonding) to a tooth structure. While particularly useful as orthodontic adhesives, these hardenable and hardened adhesives may also be used, for example, as dental adhesives, cements (e.g., glass ionomer cements, resin-modified glass ionomer cements, and orthodontic cements), and combinations thereof. Each of the above components (fillers, hardenable components, hardeners, and optional additives) shall be highlighted and described in greater detail in the sub-headings that follow.

Fillers

Polymeric Fillers

Adhesives according to the present invention contain at least one polymeric filler with a controlled particle size (the largest dimension of a particle, typically the diameter) and particle size distribution. Particles may be spherical, flat, rod-like, or some other asymmetrical shape. The particle size distribution may be unimodal or polymodal (e.g., bimodal). Preferably, the median particle size of the filler is 18 micrometers or less, more preferably 17 micrometers or less, and most preferably 16 micrometers or less. Preferably, the median particle size of the filler is greater than 6 micrometers, more preferably greater than 7 micrometers, and most preferably greater than 8 micrometers.

Figure 1:
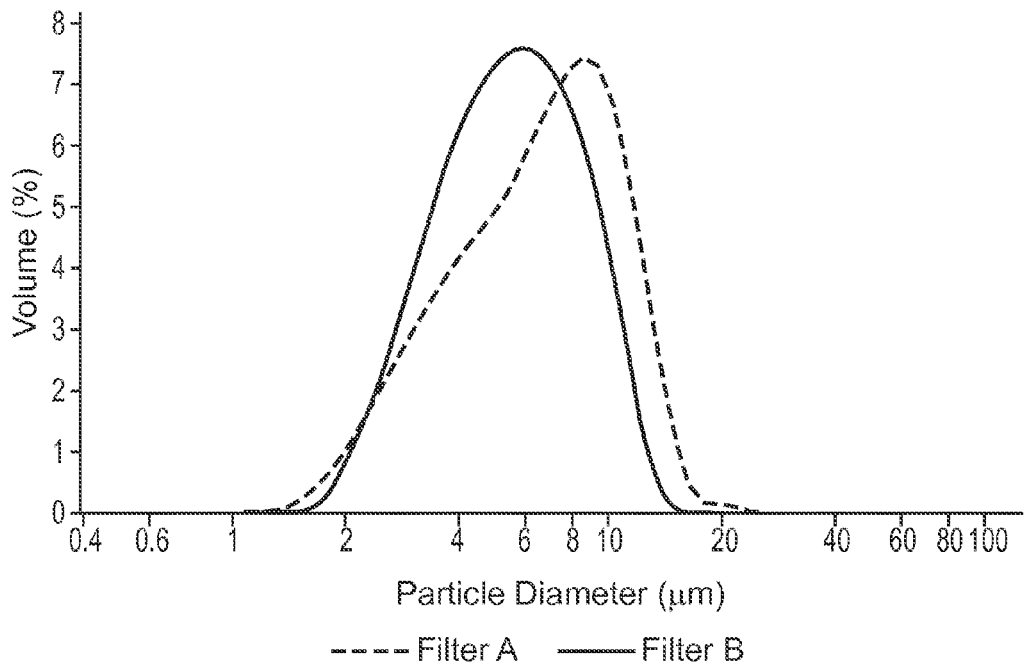
FIG. 1 is a histogram displaying the particle size distribution for a polymeric filler used in an exemplary embodiment of the invention.

The breadth of the particle size distribution on the low end of the range can be described by the ratio of the median particle size ("d50") to the 25th percentile particle size ("d25"), or d50/d25. A large d50/d25 ratio is generally indicative of a broad particle size distribution, while conversely a small d50/d25 ratio is generally indicative of a narrow particle size distribution. Preferably, d50/25 is less than 2.5, more preferably d50/25 is less than 2.0, and most preferably d50/d25 is less than 1.8. An exemplary particle size histogram is shown in FIG. 1 for two polymer fillers, A and B, that demonstrate the above characteristics. As shown, filler A has a particle size median (or d50) of 6.7 micrometers and a d50/d25 ratio of 1.55, while filler B has a median particle size (or d50) of 5.5 micrometers and a d50/d25 ratio of 1.40.

The ranges set out above reflect that the presence of some large and small particles can be acceptable. However, it is preferable that the adhesive does not contain polymer filler particles that are so large that they interfere with the proper seating of the bracket on the tooth during a bonding procedure. On the other hand, an adhesive loaded with too many small polymer particles often has a low cohesive strength. The polymeric filler is preferably present in a range from 50 percent by weight to 70 percent by weight, and more preferably from 55 percent by weight to 65 percent by weight, based on the overall weight of the adhesive.

Polymeric fillers may include natural and synthetic polymers and copolymers, such as polymethacrylic polymers, polystyrene, polycyanoacrylates, polytetrafluoroethylene, polycarbonates, polyamides, nylons, polyester, polyolefin, polyvinylchloride, polyepoxides and polyurethanes. Preferably, polymer particles are formed by emulsion polymerization or suspension polymerization. These methods are advantageous because they allow particle size characteristics to be controlled with reasonable precision. However, polymeric fillers may be formed using other methods that also allow adequate control of particle size and particle size distribution. For example, a liquid monomer may be sprayed into air and airborne spray droplets crosslinked using actinic radiation or electron beam radiation. Polymerization need not be radiation induced. For example, a cyanoacrylate monomer may be sprayed into a moist environment and polymerized in microdroplet form to produce tiny polymer beads. Moreover, polymeric fillers may be polymerized in bulk form, and then post-processed to form finely divided particles. For example, a bulk polymer may be pulverized by ball milling, shearing or by atomization, and passed through filters as needed to produce polymer particles with the proper size distribution. Particles that are formed need not be spherical.

In preferred embodiments, the polymeric filler is dimensionally stable and includes polymers which are rigid due to their being crosslinked or semi-crystalline. As another option, it is possible to use a polymer that has a high glass transition temperature, such as polystyrene or polymethyl methacrylate. In this case, it is preferable that the glass transition temperature is well above any temperature that is encountered in the oral cavity. Optionally, a resilient block copolymer such as KRATON™ or other self-organizing polymeric structure may be used, in which thermodynamic crosslinks impart dimensional stability, or creep resistance, to the polymer filler.

Polymeric fillers may also include a coated or functionalized surface to enhance the bond between the filler and the hardenable component, or resin. Crosslinked particles, for example, may optionally contain free radically polymerizable groups on the surface of the particles. For example, carbon-based plasma can be used to deposit densely packed coatings of amorphous materials comprising carbon and further optionally comprising hydrogen, nitrogen, oxygen, fluorine, silicon, sulfur, titanium, and copper onto filler particles. Depending on the hardenable component chosen, the coating could be used to optimize the interfacial compatibility between the particle and resin. Methods of plasma treatment that use an ion sheath in a capacitively coupled system may also be used to modify the hydrophilicity of polymer fillers for improved wetting by polar and/or aqueous resin components. Sources of species for hydrophilizing plasma treatments include acrylic and methacrylic acid, acrylamides, methacrylamides, maleic and fumaric acid, vinyl ethers, pyrollidones, alcohols, glycols, each of which may be used to alter particle hydrophilicity. The resulting deposits are highly crosslinked and commonly known as plasma polymers. Other plasma treatments might include deposition of nitrides and oxides such as amorphous films of silicon nitride, silicon oxide, boron nitride, titania, aluminum nitride, aluminum oxide, etc, oxynitrides, etc. Furthermore, these might include the attachment of functional groups such as amine, hydroxyl, carboxyl, silanol, and others. Preferably, the deposition of these layers is limited to thin (<1 micrometer) films to avoid an adverse impact on cured adhesive clean up. Methods of coating particles in this manner are further described in U.S. Pat. Nos. 6,015,597, 6,197,120 and U.S. Pat. No. 6,878,419 (David, et al.), which are herein incorporated by reference in their entirety.

Fillers of the present invention are further not limited to one type of polymer filler. Mixtures of two or more polymeric fillers may be used if desired.

Hybrid Fillers

In certain embodiments, it is preferable for the adhesive to be essentially free of any non-polymeric (e.g., inorganic) fillers. However, it is possible for inorganic fillers to be used together with polymeric fillers in an adhesive formulation and still obtain certain benefits, including easy adhesive clean up. For example, a small amount of particulate inorganic glass or crystal may be mixed together with a polymeric filler to form a hybrid filler system. The inclusion of an inorganic filler component may be used to impart desirable properties to the adhesive. As will be described later, inorganic fillers can be used to impart a fluoride releasing property to the adhesive. Fluoride release is a desirable feature to many orthodontists. Inorganic fillers may also be effective in increasing the modulus or strength of the adhesive or modifying its rheological properties to facilitate handling by the clinician or orthodontic assistant.

The amounts in which inorganic fillers may be added to the composition, however, depend in part on the nature of the inorganic filler. If relatively soft inorganic fillers are selected, significant amounts may be tolerated in the adhesive composition without unduly compromising ease of adhesive cleanup. Hard fillers, however, such as those with a Mohs hardness of at least 5, may adversely impact the ease of adhesive cleanup if added in significant quantities. In cases where inorganic fillers have a Mohs hardness of at least 5, it is preferred that the inorganic component constitutes 5 percent or less of the total weight of the adhesive. More preferably, any inorganic components with a Mohs hardness of at least 5 constitutes 2 percent or less of the total weight of the adhesive. Most preferably, and for the reasons set out above, the adhesive does not contain any fillers with a Mohs hardness of at least 5. In certain embodiments, the adhesive does not contain any fillers with a Mohs hardness of at least 6, or fillers with a Mohs hardness of at least 7, or fillers with a Mohs hardness of at least 8, or fillers with a Mohs hardness of at least 9. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 and TS-720 silica from Cabot Corp., Tuscola, Ill.).

Preferred non-acid-reactive filler particles include quartz (i.e., silica), submicron silica, zirconia, submicron zirconia, and non-vitreous microparticles of the type described in U.S. Pat. No. 4,503,169 (Randklev). Mixtures of these non-acid-reactive fillers are also contemplated, as well as combination fillers made from organic and inorganic materials.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened adhesive will form when the glass is mixed with the components of the adhesive. In fluoride releasing adhesives, the glass typically contains sufficient elutable fluoride ions so that the hardened adhesive will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth. Preferably, the FAS glass is present in the adhesive in an amount up to 40% by weight, based on the overall weight of the adhesive. The total filler content (polymeric and inorganic with a Mohs hardness below 5) is preferably present in a range from 50 percent by weight to 80 percent by weight, and more preferably from 55 percent by weight to 77 percent by weight, and most preferably from 60 percent by weight to 75 percent by weight based on the overall weight of the adhesive.

Generally, the average particle size for the FAS glass is no greater than 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (available from 3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired. Further description of other compositions containing FAS glass filler is provided under the HARDENABLE COMPONENTS/GLASS IONOMERS sub-heading below.

The surface of the filler particles can also be treated with a coupling agent in order to enhance the bond between the filler and the resin. Suitable coupling agents include gamma-methacryloxypropyltrimethoxysilane, gamma-mercaptopropyltriethoxysilane, gamma-aminopropyltrimethoxysilane, and the like. Silane-treated talc filler, silane-treated kaolin filler, silane-treated clay-based filler, and combinations thereof are especially preferred in certain embodiments.

Other suitable fillers are disclosed in U.S. Pat. No. 6,387,981 (Zhang et al.) and U.S. Pat. No. 6,572,693 (Wu et al.) as well as International Pat. Application Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,156,911 (Kangas et al.) and U.S. Pat. No. 7,090,722 (Budd et al.); and U.S. Pat. Application Publication No. 2005/0256223 A1 (Kolb et al.).

Hardenable Components

Ethylenically Unsaturated Compounds

As disclosed herein, suitable adhesives may use hardenable components (e.g., photopolymerizable compounds) including ethylenically unsaturated compounds (which contain free radically active unsaturated groups). In the present invention, hardenable components are preferably present in a range from 20% to 60% by weight and more preferably in a range from 30% to 45% by weight, based on the overall weight of the adhesive. Examples of useful ethylenically unsaturated compounds include acrylic acid esters, methacrylic acid esters, hydroxy-functional acrylic acid esters, hydroxy-functional methacrylic acid esters, and combinations thereof.

The adhesives (e.g., photopolymerizable compositions) may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl(meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone(meth)acrylamide; urethane(meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The hardenable component may also contain hydroxyl groups and ethylenically unsaturated groups in a single molecule. Examples of such materials include hydroxyalkyl (meth)acrylates, such as 2-hydroxyethyl(meth)acrylate and 2-hydroxypropyl(meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis [4-(2-hydroxy-3-ethacryloxypropoxy)phenyl]propane (bis- GMA). Suitable ethylenically unsaturated compounds are also available from a wide variety of commercial sources, such as Sigma-Aldrich, St. Louis. Mixtures of ethylenically unsaturated compounds can be used if desired.

In certain embodiments hardenable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the hardenable components can be used if desired. In certain embodiments, crosslinking monomers such as UDMA may represent the entire hardenable component of the adhesive. Preferably adhesives as disclosed herein include at least 10% by weight, preferably at least 20% by weight, and more preferably at least 30% by weight ethylenically unsaturated compounds (e.g., with and/or without acid functionality), based on the overall weight of the adhesive. Moreover, adhesives as disclosed herein include at most 60% by weight, preferably at most 50% by weight, and more preferably at most 45% by weight ethylenically unsaturated compounds (e.g., with and/or without acid functionality), based on the overall weight of the adhesive.

Adhesives as disclosed herein may also include one or more hardenable components in the form of ethylenically unsaturated compounds with acid functionality. As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl(meth)acrylate (e.g., HEMA) phosphates, bis((meth)acryloxyethyl) phosphate, ((meth)acryloxypropyl)phosphate, bis((meth) acryloxypropyl)phosphate, bis((meth)acryloxy)propyloxy phosphate, (meth)acryloxyhexyl phosphate, bis((meth)acryloxyhexyl)phosphate, (meth)acryloxyoctyl phosphate, bis ((meth)acryloxyoctyl)phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, poly(meth)acrylated polyboric acid, and the like, may be used as components in the hardenable component system. Also monomers, oligomers, and polymers of unsaturated carbonic acids such as (meth) acrylic acids, aromatic(meth)acrylated acids (e.g., methacrylated trimellitic acids), and anhydrides thereof can be used. Certain compositions for use in preferred methods of the present invention include an ethylenically unsaturated compound with acid functionality having at least one P—OH moiety.

Certain of these compounds are obtained, for example, as reaction products between isocyanatoalkyl(meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Pat. Application Publication No. 2004/0206932 (Abuelyaman et al.); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Adhesives as disclosed herein can also include compositions that include combinations of ethylenically unsaturated compounds with acid functionality. Preferably the adhesives are self-adhesive and are non-aqueous. For example, such compositions can include: a first compound including at least one (meth)acryloxy group and at least one —O—P(O)(OH)$_x$ group, wherein x=1 or 2, and wherein the at least one —O—P (O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler. Such compositions are described, for example, in U.S. Provisional Application Ser. No. 60/600,658 (Luchterhandt et al.), filed on Aug. 11, 2004.

Preferably adhesives as disclosed herein include at least 10% by weight, preferably at least 20% by weight, and more preferably at least 30% by weight ethylenically unsaturated compounds with acid functionality, based on the overall weight of the adhesive. Adhesives as disclosed herein include at most 60% by weight, preferably at most 50% by weight, and more preferably at most 45% by weight ethylenically unsaturated compounds with acid functionality, based on the total weight of the adhesive.

Epoxy (Oxirane) or Vinyl Ether Compounds

Adhesives as disclosed herein may also include one or more hardenable components in the form of epoxy (oxirane) compounds (which contain cationically active epoxy groups) or vinyl ether compounds (which contain cationically active vinyl ether groups), thereby forming adhesives.

The epoxy or vinyl ether monomers can be used alone as the hardenable component in a adhesive or in combination with other monomer classes, e.g., ethylenically unsaturated compounds as described herein, and can include as part of their chemical structures aromatic groups, aliphatic groups, cycloaliphatic groups, and combinations thereof.

Examples of epoxy (oxirane) compounds include organic compounds having an oxirane ring that is polymerizable by ring opening. These materials include monomeric epoxy compounds and epoxides of the polymeric type and can be aliphatic, cycloaliphatic, aromatic or heterocyclic. These compounds generally have, on the average, at least 1 polymerizable epoxy group per molecule, in some embodiments at least 1.5, and in other embodiments at least 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, carbosilane groups, nitro groups, phosphate groups, and the like. The molecular weight of the epoxy-containing materials may vary from 58 to 100,000 or more.

Suitable epoxy-containing materials useful as the resin system reactive components for use in methods of the present invention are listed in U.S. Pat. No. 6,187,836 (Oxman et al.) and U.S. Pat. No. 6,084,004 (Weinmann et al.).

Other suitable epoxy resins useful as the resin system reactive components include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexyl-methyl) adipate. For a more detailed list of useful epoxides of this nature, reference is made to U.S. Pat. No. 6,245,828 (Weinmann et al.) and U.S. Pat. No. 5,037,861 (Crivello et al.); and U.S. Pat. No. 6,779,656 (Klettke et al.).

Other epoxy resins that may be useful in adhesives as disclosed herein include glycidyl ether monomers. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262 (Schroeder), and in "Handbook of Epoxy Resins" by Lee and Neville, McGraw-Hill Book Co., New York (1967).

Other suitable epoxides useful as the resin system reactive components are those that contain silicon, useful examples of which are described in International Pat. Application Publication No. WO 01/51540 (Klettke et al.).

Additional suitable epoxides useful as the resin system reactive components include octadecylene oxide, epichlorohydrin, styrene oxide, vinyl cyclohexene oxide, glycidol, glycidylmethacrylate, diglycidyl ether of Bisphenol A and other commercially available epoxides, as provided in U.S. Pat. Application Publication No. 2005/0113477 A1 (Oxman et al.).

Blends of various epoxy-containing materials are also contemplated. Examples of such blends include two or more weight average molecular weight distributions of epoxy-containing compounds, such as low molecular weight (below 200), intermediate molecular weight (200 to 10,000) and higher molecular weight (above 10,000). Alternatively or additionally, the epoxy resin may contain a blend of epoxy-containing materials having different chemical natures, such as aliphatic and aromatic, or functionalities, such as polar and non-polar.

Other types of useful hardenable components having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the CYCLOMER series, such as CYCLOMER M-100, M-101, or A-200 available from Daicel Chemical, Japan, and EBECRYL-3605 available from Radcure Specialties, UCB Chemicals, Atlanta, Ga.

The cationically curable components may further include a hydroxyl-containing organic material. Suitable hydroxyl-containing materials may be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights (i.e., from 32 to 200), intermediate molecular weights (i.e., from 200 to 10,000, or high molecular weights (i.e., above 10,000). As used herein, all molecular weights are weight average molecular weights.

The hydroxyl-containing materials may be non-aromatic in nature or may contain aromatic functionality. The hydroxyl-containing material may optionally contain heteroatoms in the backbone of the molecule, such as nitrogen, oxygen, sulfur, and the like. The hydroxyl-containing material may, for example, be selected from naturally occurring or synthetically prepared cellulosic materials. The hydroxyl-containing material should be substantially free of groups which may be thermally or photolytically unstable; that is, the material should not decompose or liberate volatile components at temperatures below 100° C. or in the presence of actinic light which may be encountered during the desired photopolymerization conditions for the polymerizable compositions.

Suitable hydroxyl-containing materials useful in methods of the present invention are listed in U.S. Pat. No. 6,187,836 (Oxman et al.).

The hardenable component(s) may also contain hydroxyl groups and cationically active functional groups in a single molecule. An example is a single molecule that includes both hydroxyl groups and epoxy groups.

Glass Ionomers

Adhesives as described herein may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the poly-carboxylic acid and cations leached from the glass.

The glass ionomer cements may also include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. No. 5,063,257 (Akahane et al.), U.S. Pat. No. 5,520,725 (Kato et al.), U.S. Pat. No. 5,859,089 (Qian), U.S. Pat. No. 5,925,715 (Mitra) and U.S. Pat. No. 5,962,550 (Akahane et al.). In another type of RMGI, the cement may include a polycarboxylic acid, an acrylate or methacrylate-functional monomer, and a redox or other chemical cure system, e.g., as described in U.S. Pat. No. 5,154,762 (Mitra et al.), U.S. Pat. No. 5,520,725 (Kato et al.), and U.S. Pat. No. 5,871,360 (Kato). In another type of RMGI, the cement may include various monomer-containing or resin-containing components as described in U.S. Pat. No. 4,872,936 (Engelbrecht), U.S. Pat. No. 5,227,413 (Mitra), U.S. Pat. No. 5,367,002 (Huang et al.), and U.S. Pat. No. 5,965,632 (Orlowski). RMGI cements are preferably formulated as powder/liquid or paste/paste systems, and contain water as mixed and applied. The adhesives are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Pat. No. 6,765,038 (Mitra).

Hardeners

Photoinitiator Systems

In certain embodiments, the adhesives of the present invention are photopolymerizable, i.e., the hardenable component is photopolymerizable and the hardener includes a photoinitiator (or photoinitiator system), in which irradiation with actinic radiation initiates the polymerization (or hardening) of the adhesive. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl)phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the adhesive.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the adhesive. Useful amounts of other initiators are well known to those of skill in the art.

Suitable photoinitiators for polymerizing cationically photopolymerizable compositions include binary and tertiary systems. Typical tertiary photoinitiators include an iodonium salt, a photosensitizer, and an electron donor compound as described in EP 0 897 710 (Weinmann et al.); in U.S. Pat. No. 5,856,373 (Kaisaki et al.), U.S. Pat. No. 6,084,004 (Weinmann et al.), U.S. Pat. No. 6,187,833 (Oxman et al.), and U.S. Pat. No. 6,187,836 (Oxman et al.); and in U.S. Pat. No. 6,765,036 (Dede et al.). The adhesives of the invention can include one or more anthracene-based compounds as electron donors. In some embodiments, the adhesives comprise multiple substituted anthracene compounds or a combination of a substituted anthracene compound with unsubstituted anthracene. The combination of these mixed-anthracene electron donors as part of a photoinitiator system provides significantly enhanced cure depth and cure speed and temperature insensitivity when compared to comparable single-donor photoinitiator systems in the same matrix. Such compositions with anthracene-based electron donors are described in U.S. Pat. Application Publication No. 2005/0113477 A1 (Oxman et al.).

Suitable iodonium salts include tolylcumyliodonium tetrakis(pentafluorophenyl)borate, tolylcumyliodonium tetrakis(3,5-bis(trifluoromethyl)-phenyl)borate, and the diaryl iodonium salts, e.g., diphenyliodonium chloride, diphenyliodonium hexafluorophosphate, diphenyliodonium hexafluoroantimonate, and diphenyliodonium tetrafluoroboarate. Suitable photosensitizers are monoketones and diketones that absorb some light within a range of 450 nm to 520 nm (preferably, 450 nm to 500 nm). More suitable compounds are alpha diketones that have some light absorption within a range of 450 nm to 520 nm (even more preferably, 450 nm to 500 nm). Preferred compounds are camphorquinone, benzil, furil, 3,3,6,6-tetramethylcyclohexanedione, phenanthraquinone and other cyclic alpha diketones. Most preferred is camphorquinone. Suitable electron donor compounds include substituted amines, e.g., ethyl 4-(dimethylamino) benzoate and 2-butoxyethyl 4-(dimethylamino)benzoate; and polycondensed aromatic compounds (e.g., anthracene).

The initiator system, or hardener, is present in an amount sufficient to provide the desired rate of hardening (e.g., polymerizing and/or crosslinking) For a photoinitiator, this amount will be dependent in part on the light source, the thickness of the layer to be exposed to radiant energy, and the extinction coefficient of the photoinitiator. Preferably, the hardener is present in a total amount of at least 0.01% by weight, more preferably, at least 0.03% by weight, and most preferably, at least 0.05% by weight, based on the overall weight of the adhesive. Preferably, the hardener is present in a total amount of no more than 10% by weight, more preferably, no more than 5% by weight, and most preferably, no more than 2.5% by weight, based on the overall weight of the adhesive.

Redox Initiator Systems

In certain embodiments, the adhesives of the present invention are chemically hardenable, i.e., the adhesives contain a chemically hardenable component and a chemical initiator (i.e., initiator system) that can polymerize, cure, or otherwise harden the adhesive without dependence on irradiation with actinic radiation. Such chemically adhesives are sometimes referred to as "two-part" or "self-cure" compositions and may include glass ionomer cements, resin-modified glass ionomer cements, redox cure systems, and combinations thereof.

The chemically adhesives may include redox cure systems that include a hardenable component (e.g., an ethylenically unsaturated polymerizable component) and redox agents that include an oxidizing agent and a reducing agent. Suitable hardenable components, redox agents, optional acid-functional components, and optional fillers that are useful in the present invention are described in U.S. Pat. No. 6,982,288 (Mitra et al.) and U.S. Pat. No. 7,173,074 (Mitra et al.).

The reducing and oxidizing agents should react with or otherwise cooperate with one another to produce free-radicals capable of initiating polymerization of the resin system (e.g., the ethylenically unsaturated component or hardenable component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the adhesive.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. No. 6,982,288 (Mitra et al.).

The reducing and oxidizing agents are present in amounts sufficient to permit an adequate free-radical reaction rate. This can be evaluated by combining all of the ingredients of the adhesive except for the filler, and observing whether or not a hardened mass is obtained.

Preferably, the reducing agent is present in an amount of at least 0.01% by weight, and more preferably at least 0.1% by weight, based on the total weight (including water) of the components of the adhesive. Preferably, the reducing agent is present in an amount of no greater than 10% by weight, and more preferably no greater than 5% by weight, based on the overall weight (including water) of the adhesive.

Preferably, the oxidizing agent is present in an amount of at least 0.01% by weight, and more preferably at least 0.10% by weight, based on the total weight (including water) of the components of the adhesive. Preferably, the oxidizing agent is present in an amount of no greater than 10% by weight, and more preferably no greater than 5% by weight, based on the overall weight (including water) of the adhesive.

The reducing or oxidizing agents can be microencapsulated as described in U.S. Pat. No. 5,154,762 (Mitra et al.). This will generally enhance shelf stability of the adhesive, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a adhesive such as described U.S. Pat. No. 5,154,762 (Mitra et al.).

Optional Additives

Photobleachable and Thermochromic Dyes

In some embodiments, adhesives of the present invention preferably have an initial color remarkably different than the color of the patient's tooth. Color is preferably imparted to the adhesive through the use of a photobleachable or thermochromic dye. The adhesive preferably includes at least 0.001% by weight photobleachable or thermochromic dye, and more preferably at least 0.002% by weight photobleachable or thermochromic dye, based on the total weight of the adhesive. The adhesive preferably includes at most 1% by weight photobleachable or thermochromic dye, and more preferably at most 0.1% by weight photobleachable or thermochromic dye, based on the total weight of the adhesive. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the adhesive and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the adhesive's color change is initiated using actinic radiation using, for example, a dental curing light which emits visible or near infrared (IR) light for a sufficient amount of time. The mechanism that initiates the color change in the adhesives of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a color test. Using a color test, a value of $\Delta E^*$ is determined, which indicates the total color change in a 3-dimensional color space. The human eye can detect a color change of approximately 3 $\Delta E^*$ units in normal lighting conditions. The adhesives of the present invention are preferably capable of having a color change, $\Delta E^*$, of at least 20; more preferably, $\Delta E^*$ is at least 30; most preferably $\Delta E^*$ is at least 40.

Miscellaneous Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the adhesives of the invention can contain additives such as indicators, dyes, pigments, inhibitors, accelerators, viscosity modifiers, wetting agents, buffering agents, stabilizers, and other similar ingredients that will be apparent to those skilled in the art. Viscosity modifiers include the thermally responsive viscosity modifiers (such as PLURONIC F-127 and F-108 available from BASF Wyandotte Corporation, Parsippany, N.J.) and may optionally include a polymerizable moiety on the modifier or a polymerizable component different than the modifier. Such thermally responsive viscosity modifiers are described in U.S. Pat. No. 6,669,927 (Trom et al.) and U.S. Pat. Application Publication No. 2004/0151691 (Oxman et al.).

Additionally, medicaments or other therapeutic substances can be optionally added to the adhesives. Examples include, but are not limited to, fluoride sources such as tetrabutyl ammonium tetrafluoroborate, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in adhesives. Combination of any of the above additives may also be employed. The selection and amount of any one such additive can be selected by one of skill in the art to accomplish the desired result without undue experimentation.

Packaged Articles, Kits, and Methods

Figure 2:
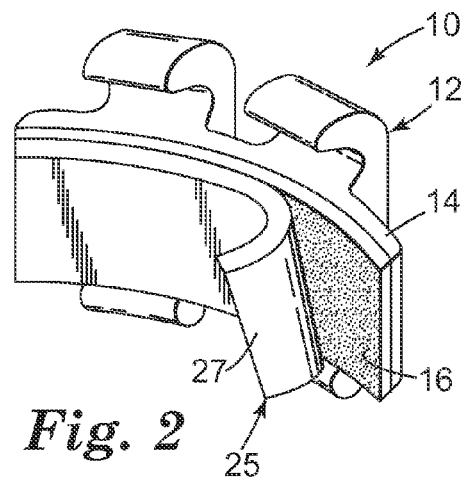
FIG. 2 is side cross-sectional view of a certain embodiment of the present invention illustrating a packaged article including an orthodontic appliance pre-coated with an exemplary adhesive thereof in a container with a removable cover.

In further embodiments, packaged appliances and kits according to the present invention include an orthodontic appliance coated with adhesives of the present invention. One such exemplary embodiment is illustrated in FIG. 2. In FIG. 2, exemplary appliance 10 includes orthodontic appliance 12 having a base 14 for bonding to a tooth structure. Exemplary appliance 12 here can represent one of a variety of orthodontic appliances including orthodontic brackets, buccal tubes, lingual buttons, lingual sheaths, cleats, and orthodontic bands. These appliances may be made of metal, plastic, ceramic and combinations thereof. Preferably the bottom surface of base 14 has a concave compound contour that matches the convex compound contours of the patient's tooth surface (not shown). Optionally the bottom surface of base 14 is provided with grooves, particles, recesses, undercuts, a chemical bond enhancement material, or any other material or structure or combination thereof that facilitates bonding the appliance 12 directly to a patient's tooth. Appliance 12 further includes an adhesive 16 in contact with base 14. Details concerning the characteristics of the adhesive 16 have already been described in detail and will not be repeated here.

It should be understood that appliance 12 can optionally include one or more additional layers of adhesives (e.g., orthodontic adhesives, orthodontic primers, or combinations thereof, which are not illustrated in FIG. 2) in contact with base 14 and/or adhesive 16. Specifically, such additional layer(s) can be between base 14 and adhesive 16; on adhesive 16 opposite base 14, or both. Such layers may or may not cover the same area, and may independently be discontinuous (e.g., a patterned layer) or continuous (e.g., non-patterned) materials extending across all or a portion of base 14.

Preferably and as shown, a release substrate 25 including a surface 27 is in contact with the adhesive 16. The release substrate 25 may be selected from a number of materials including, for example, polyolefins, poly(vinyl chloride), polyurethanes, and poly(tetrafluoroethylene). Optionally, the surface 27 of the release substrate 25 comprises a number of pores, and preferably no more than 50% by weight of the adhesive 16 is within the pores. In certain embodiments, the release substrate 25 includes closed-cell foam materials as disclosed, for example, in U.S. Pat. No. 6,183,249 (Brennan et al.).

The article 10 is preferably packaged in a container that provides barriers to the transmission of light and/or water vapor. In some embodiments of the present invention, the article 10 is preferably provided as a kit. In other embodiments, the present invention preferably provides a method of bonding an orthodontic appliance 12 to a tooth, in which the adhesive includes one or more fillers of the type described.

The adhesives of the present invention can also be adapted for indirect bonding methods. For indirect bonding methods, orthodontic appliances are typically placed, for example, on a replica model (such as one made from orthodontic stone or cured epoxy) of the patient's dental arch to provide a custom base for later mounting on the patient's tooth structure, commonly using a placement device or transfer tray. In one embodiment, the orthodontic appliances have an adhesive coated on their respective bases thereon for bonding to the replica model. Thus, the adhesive can be seated on the replica model to form a custom base, for example, upon hardening of the adhesive. Exemplary indirect bonding methods are described in greater detail in U.S. Pat. No. 7,137,812 (Cleary et al.).

Figure 3:
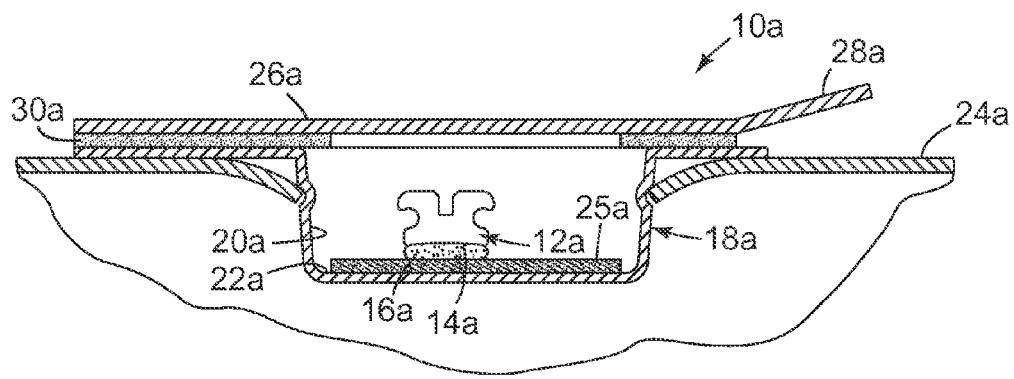
FIG. 3 is a perspective view looking at the base of an orthodontic appliance pre-coated with an exemplary adhesive that is contacted in part by a release substrate.

In another embodiment, referring to FIG. 3, the present invention provides a packaged article 10a including the orthodontic appliance 12a. The appliance 12a has a base 14a for directly bonding the appliance 12a to a patient tooth structure (not shown). The adhesive 16a extends across the base 14a of the bracket 12a. The bracket 12a and the adhesive 16a are at least partially surrounded by a container 18a. The container 18a illustrated in FIG. 3 includes an integrally-molded body with internal wall portions that define a recess or well 20a. The well 20a includes side walls and a bottom 22a. As an additional option, the side walls 30a of the well 20a include horizontally extending recesses for engagement with edge structure of carrier 24a. Additional information regarding a suitable carrier 24a is set out in U.S. Pat. No. 5,328,363 (Chester et al.). Preferably, the bottom 22a of the well 20a includes a release substrate 25a. Preferably, the article 10a also includes a cover 26a with a tab 28a, with the cover 26a being releasably connected to the container 18a by, for example, adhesive 30a.

In preferred embodiments, the package provides excellent protection against degradation of the adhesive(s) (e.g., photopolymerizable compounds), even after extended periods of time. Such containers are particularly useful for embodiments in which the adhesive optionally includes dyes that impart a color changing feature to the adhesive, as described previously. Such containers preferably effectively block the passage of actinic radiation over a broad spectral range, and as a result, the adhesives do not prematurely lose color during storage.

In preferred embodiments, the container 18a comprises a polymer and metallic particles. As an example, the container 18a may be made of polypropylene that is compounded with aluminum filler or receives an aluminum powder coating as disclosed, for example, in U.S. Patent Publication No. 2003/0196914 A1 (Tzou et al.). The combination of polymer and metallic particles is highly effective in blocking the passage of actinic radiation to color changing dyes, even though such dyes are known to be highly sensitive to light. Such containers also exhibit good vapor barrier properties. As a result, the rheological characteristics of the adhesive(s) are less likely to change over extended periods of time. For example, the improved vapor barrier properties of such containers provide substantial protection against degradation of the handling characteristics of adhesives so that the adhesives do not prematurely cure or dry or become otherwise unsatisfactory. Suitable covers 26 for such containers can be made of any material that is substantially opaque to the transmission of actinic radiation so that the adhesives do not prematurely cure. Examples of suitable materials for cover 26 include laminates of aluminum foil and polymers. For example, the laminate may comprise a layer of polyethyleneterephthalate, adhesive, aluminum foil, adhesive and oriented polypropylene.

In some embodiments, a packaged appliance can include a set of two or more orthodontic appliances, wherein at least one of the appliances has an adhesive thereon. Additional examples of appliances and sets of appliances are described in U.S. Patent Application Publication No. 2005/0133384 A1 (Cinader et al.). Packaged orthodontic appliances are described, for example, in U.S. Pat. Application Publication No. 2003/0196914 A1 (Tzou et al.) and U.S. Pat. No. 4,978,007 (Jacobs et al.), U.S. Pat. No. 5,015,180 (Randklev), U.S. Pat. No. 5,328,363 (Chester et al.), and U.S. Pat. No. 6,183,249 (Brennan et al.).

Still another embodiment provides a method for removing the adhesive from the surface of a tooth. In this method, a tooth surface is provided and a hardened adhesive of the present invention resides on at least a portion of the tooth surface thereon. The term "tooth" in this case may represent not only a patient's actual tooth but also a physical replica of a patient's tooth such one provided by an orthodontic stone or cured epoxy model. The method further includes applying an abrasive to the tooth surface to remove the cured adhesive from the tooth, wherein the abrasive has a Mohs hardness that is less than 5. In certain embodiments, the abrasive has a Mohs hardness that is less than 4.5, or less than 4, or less than 3.5.

This abrasive can take the form of an abrasive particle that is coated on a substrate, such as a finishing disk or gritted sandpaper. One example of a suitable coated abrasive is a SOF-LEX finishing disks from 3M Company in St. Paul, Minn. For a finishing disk, a rotation speed of 10,000 rpm can be used. As an alternative, it is possible to use prophylactic (or prophy) treatment, which is commonly used to clean the teeth of a patient prior to bonding. Prophy treatment may include pumice powders such as those available from dental distributors. Fine, medium or coarse grain pumice (prophy paste), along with a prophy cup and prophy angle, can be used. A finishing burr or an edged dental hand instrument, such as a scalar, could also be used.

Objects and advantages of this invention are further illustrated by the following examples. Particular materials and amounts thereof recited in these examples, as well as other conditions and details, however, should not be construed to unduly limit this invention. Unless otherwise indicated, all parts and percentages are on a weight basis, all water is deionized water, and all molecular weights are weight average molecular weight. Unless otherwise noted, all reagents were obtained from Sigma-Aldrich Corp. in St. Louis, Mo.

EXAMPLES

As used herein,
"BisGMA" refers to 2,2-bis[4-(2-hydroxy-3-methacryloyloxypropoxy)phenyl]propane;
"BisEMA" refers to ethoxylated (2 mole ethylene oxide) bisphenol A dimethacrylate
"BHT" refers to 2,6-Di-tert-butyl-4-methylphenol;
"CPQ" refers to camphorquinone;
"EDMAB" refers to ethyl-4-(N,N-dimethylamino)benzoate;
"Iodonium $PF_6^-$" refers to iodonium hexafluorophosphate;
"HEMA" refers to 2-hydroxyethyl methacrylate;
"TEGDMA refers to tetraethylene glycol dimethacrylate;
"UDMA" refers to urethane dimethacrylate;
"SR340" refers to 2-phenoxyethyl methacrylate, available from Sartomer Company, Inc. in Exton, Pa.;

"PMMA" refers to crosslinked poly(methyl methacrylate) filler, prepared and described in Comparative Example 8 in U.S. Pat. No. 5,238,736 (Tseng et al.);

"PSt" refers to poly(styrene) filler, prepared and described in Comparative Example 9 in U.S. Pat. No. 5,238,736 (Tseng et al.);

"P(St-EMA)" refers to poly(styrene-r-ethyl(methacrylate)) copolymer filler, prepared using methods disclosed in U.S. Pat. No. 5,238,736 (Tseng et al.);

"MRD PMMA 20-1", "MRD PMMA 20-3" refer to poly (methyl methacrylate) fillers with two different particle size distributions, prepared using methods disclosed in U.S. Pat. No. 5,238,736 (Tseng et al.);

"MR-2HG" refers to 2 micrometer diameter PMMA microparticles available from Soken Inc. in Tokyo, JAPAN;

"MR-7HG" refers to 7 micrometer diameter PMMA microparticles available from Soken Inc. in Tokyo, JAPAN;

"MR-10HG" refers to 10 micrometer diameter PMMA microparticles available from Soken Inc. in Tokyo, JAPAN;

"MR-7G" refers to 7 micrometer diameter PMMA microparticles (with reduced crosslinking) available from Soken Inc. in Tokyo, JAPAN;

"S/T Schott Glass" refers to silane-treated fluoroaluminosilicate glass prepared and described in Preparatory Example 1 in International Patent Application Publication No. WO 00/69393 (Brennan et al.);

"Finely divided PMMA" refers to poly(methyl methacrylate) filler pulverized from bulk poly(methyl methacrylate) powder with a molecular weight of 15,000 g/mol;

"S/T Concise filler" refers to silane-treated quartz filler, prepared and described in U.S. Pat. No. 6,960,079 (Brennan et al.) as "Filler A".

Shear Bond Strength Test

All shear bond strength measurements were conducted on uncut bovine teeth, which were cleaned and partially embedded in circular polymethylmethacrylate discs with the labial tooth surface exposed. All teeth underwent further prophy treatment for 30 seconds using Oral-B brand medium-sized pumice powder (from Patterson Companies, Inc. in St. Paul, Minn.), rinsing with water and drying using an air syringe immediately prior to bonding. The dry enamel was then etched and primed by rubbing TRANSBOND PLUS brand Self Etching Primer (available from 3M Unitek in Monrovia, Calif.) on the teeth using the provided microbrush. A gentle air burst was used to thinly spread and dry the primer on the tooth surface to be bonded. Approximately 10 mg of test adhesive was then applied to the base of a VICTORY SERIES brand upper central low profile bracket (part no. 024-775, from 3M Unitek in Monrovia, Calif.), and the coated bracket firmly seated onto the tooth surface. Excess adhesive expressed around the periphery of the bracket base was subsequently removed using a 0/1 Marquette Condenser (part no. PLG 0/1, from Hu-Friedy in Chicago, Ill.), taking care not to inadvertently disturb the bracket position. The adhesive was then photocured by exposure to actinic radiation using a 3M ESPE ELIPAR brand TRILIGHT curing light unit (from 3M ESPE in St. Paul, Minn.) for 10 seconds on two opposite sides of the bracket. The above process was repeated for as many bonding test specimens as needed to obtain a complete set of replicated samples. After all specimens were fully bonded, they were submerged in water maintained at 37° C. for 24 hours.

Debonding was conducted on each test specimen using an R-5500 Universal Test Machine (from Instron in Norwood, Mass.) outfitted with a 500 N load cell. For each debonding, the test specimen was mounted in a fixture, then a 0.44 mm (0.017 inches) diameter stainless steel wire fixed to a crosshead was looped beneath the occlusal tiewings of the bracket and the crosshead was translated upwards at 5.1 mm (0.20 inches) per minute until shear failure was observed. Raw force data were converted to force per unit area (units of $kg/cm^2$ or MPa) using the known bracket base area (10.6 $mm^2$, or 0.0164 $inches^2$, for VICTORY SERIES brand upper central low profile brackets). For each adhesive tested, the mean and standard deviation of shear bond strength were reported for a set of at least 5 replicated test measurements. To maintain consistency during testing, all adhesives within a series were conducted side-by-side by a single operator, and ambient temperature and humidity were held as constant as possible throughout the test.

In some cases and when noted, the VICTORY SERIES brand brackets above were substituted by other orthodontic brackets, such as CLARITY MBT brand upper left central ceramic brackets (P/N 6400-801, from 3M Unitek in Monrovia, Calif.) or MINI-DIAMOND brand lower right central brackets (part no. 455-0610, from Ormco Corporation in Glendora, Calif.). The procedure was otherwise identical.

Particle Size Measurement

The size mean and size distribution of filler particles was obtained using a Model LS 13 320 particle size analyzer, from Beckman-Coulter in Fullerton, Calif. A typical procedure was to disperse 100 milligrams of filler powder in a 1% aqueous CALGON brand solution with 10 drops of LIQUI-NOX brand detergent (from Alconox Inc. in White Plains, N.Y.). The suspension is exposed to high intensity ultrasonic sound waves using an ultrasonic horn for 60 seconds. The dispersions warm up during this time and kept in vials on a rotating stage to prevent settling. Data collection was carried out on the particle size analyzer using these dispersions. Data analysis was conducted using manufacturer supplied software that uses Fraunhofer equations which do not require inclusion of refractive index in the calculations, or using a polarization intensity differential scattering (PIDS) model that incorporates the refractive index. Particle size data was reported as the median particle size ($d_{50}$) using volume distribution rather than radius distribution for the particles. All reported values represent the average of 3 replicated particle size measurements.

Buehler Abrasion Testing

To evaluate the ease of removing cured adhesive from the enamel surface following the debonding of an orthodontic appliance, abrasion testing was conducted on rectangular coupons of cured adhesive. To prepare and photocure these rectangular coupons, uncured adhesive paste was pressed into a stainless steel mold with an inner chamber sized at 2.1 cm (0.83 in.) by 1.5 cm (0.59 in.) by 0.183 cm (0.0720 in.). Each coupon was pressed into the mold using a Carver Model 3912 laboratory press (Carver, Inc. in Wabash, Ind.) at a pressure of 5000 psi (34.47 MPa) for 60 seconds. Immediately thereafter, the adhesive was photocured by irradiating in the press for 120 seconds using tungsten halogen light, followed by a high intensity pulsed Xenon light source (Kulzer UniXS in Hanau, GERMANY). After subsequent removal from the mold, the coupon was again irradiated, approximately 2.5 cm (1 in.) away from the light source, for 90 seconds on each side using the high intensity pulsed xenon light source to obtain a more complete cure.

A pair of coupon specimens were weighed and then mounted on the rotary platen of a Buehler Grinder-Polisher Model 49-1775-160 (from Buehler, Ltd. in Lake Bluff, Ill.) at diametrically opposed locations such that the long side of the specimen was oriented perpendicular to the direction of rotation. Double-sided foam tape (from 3M Company, St. Paul) was used to attach the specimens to the rotary platen. A fresh 12 in. (30.5 cm) diameter pad of 3M Wet-or-Dry brand 600 grit sandpaper (from 3M Company, St. Paul, Minn.) was used for abrasion testing and was mounted onto the stationary stage of the instrument. The contact load was set to 10 lbs. (44.5 N) and the rotary platen was set to rotate at 150 rpm for 30 seconds with a stream of water directed to flow continuously across the face of the 600 grit sandpaper. After 60 seconds of abrasion testing had elapsed, the rotary platen was stopped, the specimen carefully removed from the double-sided sticky tape and weighed again to record the change in mass and calculate the percentage loss. Reported values were determined as the mean percent loss value measured from 2 replicated measurements.

Examples 1-3 and Comparative Example CE-1

In the first series, Examples 1-3 were intended to probe the effect of filler loading on shear bond strength. During adhesive preparation, adhesive components were stored and handled under yellow lights to minimize premature polymerization. For each of Examples 1-3, the initiator system was first prepared by combining amounts of camphorquinone, EDMAB, and iodonium $PF_6^-$ with the hardenable components SR340 and UDMA. Quantities of the above components are given in Table 1. The adhesive pastes were alternately heated in a convection oven at 85° C. and homogenously mixed in a DAC-150FZ SpeedMixer (from Flacktec Inc. in Landrum, S.C.) at 3000 rpm for 5 cycles at 60 seconds. This cycle was repeated until a homogenous resin mixture was obtained. As shown, filler loadings ranged from 59.9 to 62.4 percent by weight based on the overall weight of the adhesive. Finally, the resin mixture was split into three batches and a polymeric filler, MR-7HG, added to each to form three adhesive pastes with various filler loadings. MR-7HG is a PMMA emulsion-polymerized filler with a nominal median particle size of 7 micrometers. Shear bond strength, as measured on metal orthodontic brackets, was then conducted according to the Shear Bond Strength Test method described earlier. The MR-7HG particle size was also characterized using the Particle Size Measurement method described earlier. These results are shown at the bottom of Table 1. TBXT adhesive paste, labeled as comparative example CE-1, was used as a benchmark adhesive and tested side to side with Examples 1-3. While some differences in mean bond strength were observed, the adhesives in Examples 1-3 yielded mean shear bond strengths that were similar to each other and comparable to that of TBXT. This result demonstrates that orthodontic adhesives containing polymeric fillers can achieve bond strengths comparable to commercially available orthodontic adhesives.

Examples 4-6 and Comparative Example CE-2

Examples 4-6 were intended to probe the effect of particle size on shear bond strength, with filler loading held approximately constant. Each of Examples 4-6 was prepared as before by mixing together quantities of camphorquinone, EDMAB, and Iodonium $PF_6^-$, along with SR340 and UDMA as shown in Table 1. In this case, however, three different PMMA filler diameters were examined. Particle sizes corresponding to the fillers MR-2HG, MR-7HG, and MR-10HG were measured and listed at the bottom of Table 1. These fillers were homogenously blended into the adhesive paste at filler loadings of approximately 57, 60, and 59 weight percent, respectively. Shear bond strength testing then proceeded on these compositions and the results compared with those of a TBXT control adhesive, labeled Comparative Example CE-2. The bond strength testing on these materials revealed that that 6.71 micrometer particle size (Example 5) provided the highest mean bond strength, while the 2.72 micrometer particle size (Example 4) provided the lowest. Statistical analysis furthermore demonstrated that the difference between these two compositions was significant (P=0.006). Examples 5 and 6 yielded similar bond strengths similar to, or even slightly exceeding, that of Comparative Example CE-2.

Examples 7-9 and Comparative Example CE-3

In Examples 7-9, formulations combining PMMA particles with different hardenable components, or resin systems, were prepared and tested for differences in shear bond strength. Example 7 used a resin system based on BisGMA, BisEMA, and SR340, while Examples 8 and 9 used a resin system based on UDMA and SR340. Compositions for these materials are listed in Table 2. Bond strength data, also shown in Table 2, was benchmarked to TBXT, or Comparative Example CE-3.

Depending on the resin type and viscosity, the maximum loading of PMMA particles achievable was slightly different in this series of experiments. The maximum useful loading of particles in Example 7 is 45% by weight, while the maximum useful loading in Examples 8 and 9 is near 60% by weight. This has a direct effect on the rheology of the adhesive paste.

TABLE 1

Compositions and shear bond strength data for Examples 1-6 and Comparative Examples CE-1, CE-2

| Component | Example | | | | | | | |
|---|---|---|---|---|---|---|---|---|
| | 1 | 2 | 3 | CE-1 (TBXT) | 4 | 5 | 6 | CE-2 (TBXT) |
| CPQ | 0.18% | 0.17% | 0.20% | | 0.21% | 0.20% | 0.20% | |
| EDMAB | 0.36% | 0.34% | 0.39% | | 0.42% | 0.39% | 0.40% | |
| Iodonium $PF_6^-$ | 0.19% | 0.18% | 0.20% | | 0.22% | 0.20% | 0.21% | |
| SR340 | 14.8% | 13.7% | 15.7% | | 16.8% | 15.7% | 16.2% | |
| UDMA | 22.1% | 20.6% | 23.6% | | 25.3% | 23.6% | 24.1% | |
| MR-2HG | | | | | 57.1% | | | |
| MR-7HG | 62.4% | 65.0% | 59.9% | | | 59.9% | | |
| MR-10HG | | | | | | | 58.9% | |
| Median particle size (micrometers) | 6.71 | 6.71 | 6.71 | | 2.72 | 6.71 | 9.93 | |

TABLE 1-continued

Compositions and shear bond strength data for Examples 1-6 and Comparative Examples CE-1, CE-2

| Component | 1 | 2 | 3 | CE-1 (TBXT) | 4 | 5 | 6 | CE-2 (TBXT) |
|---|---|---|---|---|---|---|---|---|
| Shear bond strength, mean (MPa) | 12.68 | 12.46 | 15.78 | 14.21 | 8.40 | 16.54 | 14.73 | 14.65 |
| Shear bond strength, standard deviation (MPa) | 4.50 | 2.19 | 3.35 | 2.03 | 0.39 | 3.48 | 1.08 | 2.10 |

Overall, measured bond strengths were similar or slightly higher than those of Comparative Example CE-3.

Examples 10-11 and Comparative Example CE-4

In Examples 10-11, a comparison was made between adhesives with similar PMMA particle size and filler loading, but different levels of filler crosslinking MR-7HG, used in Example 10, and MR-7G, used in Example 11, both have nominal particle sizes around 7 micrometers. The former, however, has approximately twice the degree of crosslinking as the latter. All compositions are provided in Table 2. As before, shear bond strength measurements were conducted and the results compared with TBXT in Comparative Example CE-4.

The data suggests that increasing the level of crosslinker used in the emulsion polymerized filler has a significant positive effect on shear bond strength. Differences in bond strength between Examples 10 and 11 were further determined to be significant (P=0.048). The adhesive used in Example 11 displayed a mean bond strength slightly lower than that of Comparative Example CE-4, although the standard deviation was also lower.

Examples 12-15 and Comparative Example CE-5

The purpose of Examples 12-15 is to demonstrate the difference in abrasion test performance between an adhesive using a PMMA filler (Example 12), adhesives using a hybrid PMMA/inorganic glass filler (Examples 13-15) and a benchmark adhesive, TBXT (Comparative Example CE-5). Using the earlier described Buehler Abrasion Test Method, the formulations for Examples 12-15 given in Table 3 were used to prepare rectangular coupons that were weighed, then mounted onto a rotating platen and abraded for a fixed amount of time using an abrasive. The coupon specimens were then removed and re-weighed to determine the loss of mass (i.e., simulating removal of adhesive residue at the end of orthodontic treatment). In this test, Examples 12-15 each contained MR-7HG filler, with Examples 13-15 additionally including S/T Schott Glass filler in amounts ranging from 0 to 40% by weight.

TABLE 2

Compositions and shear bond strength data for Examples 7-11 and Comparative Examples CE-3, CE-4

| Component | 7 | 8 | 9 | CE-3 (TBXT) | 10 | 11 | CE-4 (TBXT) |
|---|---|---|---|---|---|---|---|
| CPQ | 0.14% | 0.20% | 0.19% | | 0.14% | 0.14% | |
| EDMAB | 0.56% | 0.39% | 0.39% | | 0.56% | 0.56% | |
| Iodonium $PF_6^-$ | 0.34% | 0.20% | 0.21% | | 0.34% | 0.34% | |
| SR340 | 5.4% | 15.7% | 8.0% | | 5.4% | 5.4% | |
| UDMA | | 23.6% | 31.2% | | | | |
| BisGMA | 29.3% | | | | 29.4% | 29.3% | |
| BisEMA | 19.1% | | | | 19.2% | 19.1% | |
| BHT | 0.05% | | | | 0.05% | 0.05% | |
| MR-7G | | | | | 45.0% | | |
| MR-7HG | 45.0% | 59.9% | 60.0% | | | 45.1% | |
| Shear bond strength, mean (MPa) | 18.12 | 19.14 | 17.50 | 16.65 | 10.6 | 15.0 | 19.7 |
| Shear bond strength, standard deviation (MPa) | 1.50 | 1.58 | 4.07 | 3.31 | 3.1 | 2.9 | 7.3 |

The abrasion test results are shown in Table 3. This data shows a very substantial difference in the ease of adhesive cleanup, with Example 12 achieving 100% removal of the adhesive residue and CE-5 achieving only 5.3% removal. Increasing the amount of the S/T Schott Glass inorganic filler had the effect of decreasing the ease of cleanup as shown by Examples 13-15. Nonetheless, these results show that even with up to 40% by weight of an inorganic fluoroaluminosilicate filler such as S/T Schott Glass, it is possible to obtain significantly better adhesive cleanup than the Comparative Example CE-5. This example furthermore demonstrates that it may be possible to obtain fluoride release in combination with easy cleanup. As such, these organic fillers appear to be compatible with other properties desired by the dental or orthodontic clinician.

Examples 16-18 and Comparative Example CE-6

In Examples 16-18, adhesive compositions similar to those used in Examples 12, 14, and 15 were evaluated for shear bond strength and compared with TBXT (Comparative Example CE-6). The compositions of these adhesives and the corresponding shear bond strength data are shown in Table 4.

The shear bond strength data for Examples 16-18 show mean bond strengths consistently exceeding 15 MPa, although these were lower than the Comparative Example CE-6, which produced unusually high bond strength data exceeding 22 MPa. It was also noted that the data sets corresponding to Examples 16-18 were statistically equivalent (P 0.191). Therefore, increasing the amount of S/T Schott Glass filler did not appear to have an adverse effect on bond strength. This result demonstrates that it may be possible to introduce inorganic fluoride releasing glasses into these exemplary adhesives with little or no significant negative impact on either bond strength or ease of adhesive removal.

TABLE 3

Composition and abrasion test data for Examples 12-15 and Comparative Example CE-5

| Component | 12 | 13 | 14 | 15 | CE-5 (TBXT) |
|---|---|---|---|---|---|
| CPQ | 0.16% | 0.17% | 0.17% | 0.17% | |
| EDMAB | 0.41% | 0.35% | 0.34% | 0.34% | |
| Iodonium $PF_6^-$ | 0.22% | 0.17% | 0.17% | 0.17% | |
| SR340 | 14.4% | 13.7% | 13.7% | 13.7% | |
| UDMA | 21.7% | 20.6% | 20.6% | 20.5% | |
| MR-7HG | 63.1% | 55.0% | 44.9% | 24.8% | |
| S/T Schott glass | | 10.0% | 20.1% | 40.3% | |
| % mass loss, mean | 100% | 90.1% | 85.4% | 77.8% | 5.3% |
| % mass loss, standard deviation | 0.0% | 5.2% | 3.6% | 4.6% | 0.3% |

TABLE 4

Composition and shear bond strength data for Examples 16-18 and Comparative Examples CE-6

| Component | 16 | 17 | 18 | CE-6 (TBXT) |
|---|---|---|---|---|
| CPQ | 0.20% | 0.15% | 0.11% | |
| EDMAB | 0.39% | 0.30% | 0.23% | |
| Iodonium $PF_6^-$ | 0.20% | 0.15% | 0.11% | |
| SR340 | 23.5% | 11.8% | 9.0% | |
| UDMA | 15.7% | 17.6% | 13.6% | |
| MR-7HG | 60.1% | 50.0% | 36.9% | |
| S/T Schott glass | | 20.0% | 40.1% | |
| Shear bond strength, mean (MPa) | 16.89 | 16.95 | 18.06 | 22.32 |
| Shear bond strength, standard deviation (MPa) | 7.33 | 2.49 | 3.06 | 3.31 |

Examples 19-24 and Comparative Example CE-7

In Examples 19-24, three different emulsion-polymerized filler compositions were examined, including two homopolymers, PMMA and PSt, as well as a copolymer, P(St-EMA). These polymeric fillers were incorporated into exemplary adhesive formulations and shear bond strength measured to compare them with each other and TBXT (Comparative Example CE-7). As shown by the adhesive compositions in Table 5, each polymeric filler was blended at two filler loadings, 40% and 50-54%, based on the overall weight of the adhesive, to produce Examples 19-24. The effect of particle size was minimized by selecting fillers with similar particle diameters, ranging from 4-7 micrometers.

From the bond strength data shown at the bottom of Table 5, it is evident that a number of different polymeric fillers may be effectively used to produce acceptable bonds strengths. Bond strength data were found to be statistically similar to, or slightly lower than, those of the Comparative Example. This data also demonstrates the extent to which filler loading affects shear bond strength. In this series, the filler loading around 40% yielded bond strength values superior to the filler loading around 50-54%. However, it was noted that compositions with the 40% loading tended to produce adhesive handling properties that were less viscous than compositions with the 50-54% filler loading.

Examples 25 and Comparative Example CE-8, CE-9

The purpose of Example 25 is to compare adhesives containing emulsion polymerized PMMA filler, which has a generally narrow particle size distribution, to a finely divided PMMA filler, which has a broad particle size distribution. MR-7HG was used as the emulsion polymerized filler in Example 25, while PMMA powder (MW=15,000 g/mol), pulverized with a mortar and pestle, was used as the finely divided filler in Comparative Example CE-8. TBXT was used as a second Comparative Example CE-9. Table 6 lists the compositions used to prepare these materials and measured filler particle sizes, along with the shear bond strength results corresponding to each composition.

TABLE 5

Composition and shear bond strength data for Examples 19-24 and Comparative Example CE-7

| Component | 19 | 20 | 21 | 22 | 23 | 24 | CE-7 (TBXT) |
|---|---|---|---|---|---|---|---|
| CPQ | 0.12% | 0.15% | 0.12% | 0.15% | 0.12% | 0.15% | |
| EDMAB | 0.46% | 0.59% | 0.47% | 0.59% | 0.49% | 0.60% | |

TABLE 5-continued

Composition and shear bond strength data for
Examples 19-24 and Comparative Example CE-7

| Component | Example 19 | 20 | 21 | 22 | 23 | 24 | CE-7 (TBXT) |
|---|---|---|---|---|---|---|---|
| Iodonium $PF_6^-$ | 0.28% | 0.36% | 0.28% | 0.36% | 0.30% | 0.36% | |
| BisGMA | 27.4% | 35.3% | 28.0% | 35.2% | 29.3% | 35.6% | |
| BisEMA | 17.9% | 23.0% | 18.3% | 23.0% | 19.1% | 23.3% | |
| BHT | 0.05% | 0.06% | 0.05% | 0.06% | 0.05% | 0.06% | |
| PMMA filler, lightly crosslinked, 7 μm | 53.8% | 40.5% | | | | | |
| pSt filler, lightly xlinked, 4.6 μm | | | 52.8% | 40.6% | | | |
| p(St-r-EMA) filler, lightly xlinked, 4-5 μm | | | | | 50.6% | 40.0% | |
| Shear bond strength, mean (MPa) | 8.5 | 11.9 | 8.9 | 10.8 | 7.4 | 9.9 | 12.1 |
| Shear bond strength, standard deviation (MPa) | 2.9 | 2.4 | 1.4 | 1.9 | 2.2 | 2.0 | 1.5 |

From these bond strength results, it is shown that there is a statistically significant difference between PMMA fillers produced using these two different methods (P=0.004). The emulsion polymerized PMMA fillers provided a significant advantage over finely divided PMMA powders. While CE-9 displayed much higher bond strength than both Example 25 and CE-8, this difference can be attributable to the CE-8 values being unusually high in this series; the mean bond strength of Example 25 is still very acceptable at 14 MPa. These results also demonstrate that merely using a finely divided polymeric filler in an adhesive does not necessarily yield a useful composition.

TABLE 6

Composition and shear bond strength data for Examples
25-28 and Comparative Examples CE-8, CE-9

| Component | Example 25 | CE-8 (PMMA) | CE-9 (TBXT) |
|---|---|---|---|
| CPQ | 0.20% | 0.20% | |
| EDMAB | 0.39% | 0.39% | |
| Iodonium $PF_6^-$ | 0.20% | 0.20% | |
| SR340 | 15.7% | 15.7% | |
| UDMA | 23.5% | 23.5% | |
| MR-7HG | 60.1% | | |
| Finely divided PMMA | | 60.0% | |
| Median particle size (micrometers) | 6.71 | 85.84 | |
| Shear bond strength, mean (MPa) | 13.99 | 8.47 | 25.38 |
| Shear bond strength, standard deviation (MPa) | 2.30 | 1.76 | 6.60 |

Examples 26-29 and Comparative Example CE-10

In this series, Examples 26-29 show how introducing increasing amounts of hard silica filler into the adhesive influences the ease of adhesive clean up. Table 7 shows adhesive compositions for Examples 26-29, which contain varying levels of silica. These compositions were prepared using methods similar to those previously described for Examples 1-3. Abrasion testing was then carried out according to the Buehler Abrasion Testing method also previously described.

The abrasion test results displayed at the bottom of Table 7 reveal that there is a remarkable loss in ease of adhesive cleanup when adding even small amounts of S/T Concise filler. The addition of even 5% by weight of S/T Concise filler resulted in a reduction in adhesive removal from 100% to 28% under identical conditions. This result is in contrast to the addition of fluoroaluminosilicate glass filler in Examples 13-15, which showed a much lesser impact on ease of adhesive clean up.

Examples 33-34 and Comparative Examples CE-11, CE-12

Examples 33-34 show the measured bond strength of exemplary adhesives as used on orthodontic appliances other than VICTORY SERIES metal brackets, including ceramic orthodontic brackets and metal orthodontic brackets with an alternative mesh base. In these examples, the adhesive was prepared with the 7 micrometer diameter MR-7HG and Cab-O-Sil filler and TEGDMA/UDMA resin system based on the compositions shown in Table 8. CLARITY MBT upper left central ceramic brackets were used in Example 33, lower right Central MINI-DIAMOND brackets (available from Ormco Corporation in Glendora, Calif.) were used in Example 34, and TBXT was used in respective Comparative Examples CE-11 and CE-12.

From the bond strength data shown at the bottom of Table 8, the MR-7HG filled adhesive displayed significantly lower bond strength than TBXT when compared on ceramic brackets. However, when the comparison was made on the alternative mesh brackets, the adhesives were found to have comparable bond strength. It is also worth noting that Example 34 (displaying a standard deviation of 2.64 MPa) showed a much narrower distribution of bond strengths compared with Comparative Example CE-12 (displaying a standard deviation of 9.18 MPa). Adhesives with polymeric fillers have shown, in these examples, capable of providing bond strength at a consistency that is at least comparable to that of commercially available adhesives.

TABLE 7

Composition and shear bond strength data for Examples 26-29 and Comparative Example CE-10

| Component | 26 | 27 | 28 | 29 | CE-10 (TBXT) |
|---|---|---|---|---|---|
| CPQ | 0.18% | 0.17% | 0.17% | 0.14% | |
| EDMAB | 0.36% | 0.34% | 0.34% | 0.27% | |
| Iodonium $PF_6^-$ | 0.18% | 0.17% | 0.17% | 0.14% | |
| SR340 | 14.2% | 13.7% | 13.7% | 10.9% | |
| UDMA | 21.3% | 20.5% | 20.5% | 16.3% | |
| MR-7HG | 58.8% | 55.2% | 45.1% | 32.2% | |
| S/T Concise filler | 5.0% | 9.9% | 20.0% | 40.1% | |
| % mass loss, mean | 27.9% | 22.2% | 16.4% | 9.8% | 5.3% |
| % mass loss, standard deviation | 5.4% | 1.6% | 0.5% | 2.0% | 0.3% |

TABLE 8

Composition and shear bond strength data for Examples 33-34 and Comparative Examples CE-13, CE-14

| Component | 33 | CE-11 (TBXT) | 34 | CE-12 (TBXT) |
|---|---|---|---|---|
| CPQ | 0.19% | | 0.19% | |
| EDMAB | 0.37% | | 0.37% | |
| Iodonium $PF_6^-$ | 0.19% | | 0.19% | |
| TEGDMA | 3.75% | | 3.75% | |
| UDMA | 33.5% | | 33.5% | |
| MR-7HG | 60.0% | | 60.0% | |
| Cab-O-Sil M-5 | 2.00% | | 2.00% | |
| Bracket type | ceramic | ceramic | alternative mesh | Alternative mesh |
| Shear bond strength, mean (MPa) | 7.23 | 10.21 | 16.99 | 19.55 |
| Shear bond strength, standard deviation (MPa) | 2.32 | 2.32 | 2.80 | 9.75 |

Examples 35-38 and Comparative Examples CE-13

Examples 35-38 show the evaluation of a two adhesive formulations with median particle sizes significantly larger than the MR-7HG fillers used in previous Examples 33-34. In this series, Examples 35,37 use an MRD 20-1 PMMA filler with a monomodal size distribution around 17 micrometers, while Examples 36,38 use a blend of MRD PMMA 20-1 and MRD PMMA 20-3 fillers with a bimodal size distribution centered around 17 and 8 micrometers, respectively. All filler size data were obtained according to the particle size measurements methods previously described.

The bond strengths of these adhesives were evaluated using VICTORY SERIES brand low profile upper right central metal brackets (part no. 024-776) in Examples 35,36 and CLARITY brand standard edgewise brackets (part no. 6400-920) ceramic brackets in Examples 37,38. Measured bond strengths were benchmarked with that of TBXT on ceramic brackets in Comparative Example CE-13 (there was no comparative example on metal brackets). The measured bond strengths of all adhesives are provided in Table 9. Further included in Table 9 are the compositions, median particle sizes and d50/d25 particle size ratios for the adhesives in Examples 35-38.

Each of Examples 35-38 produced mean bond strength values exceeding that of the Comparative Example CE-13, although the bond strength distributions observed in Examples 35-38 were also wider. These examples demonstrate that the larger particle sizes used in examples 35-38 are indeed effective in bonding both metal and ceramic brackets to teeth. Comparing these examples to Examples 33-34, median particle size and particle size distribution both appear to be a significant factors that affect the performance of these filled orthodontic adhesives, particularly on ceramic appliances.

TABLE 9

Composition and shear bond strength data for Examples 33-34 and Comparative Examples CE-13, CE-14

| Component | 35 | 36 | 37 | 38 | CE-13 (TBXT) |
|---|---|---|---|---|---|
| CPQ | 0.20% | 0.19% | 0.20% | 0.19% | |
| EDMAB | 0.39% | 0.37% | 0.39% | 0.37% | |
| Iodonium $PF_6^-$ | 0.20% | 0.20% | 0.20% | 0.20% | |
| UDMA | 39.46% | 37.47% | 39.46% | 37.47% | |
| BHT | 0.04% | 0.04% | 0.04% | 0.04% | |
| MRD PMMA 20-1 | 58.76% | 30.37% | 58.76% | 30.37% | |
| MRD PMMA 20-3 | | 30.38% | | 30.38% | |
| Cab-O-Sil M-5 | 0.95% | 0.99% | 0.95% | 0.99% | |
| Bracket type | metal | Metal | Ceramic | ceramic | Ceramic |
| Median particle size (micrometers) | 16.72 | 8.25 | 16.72 | 8.25 | |
| d50/d25 | 1.15 | 1.17 | 1.15 | 1.17 | |
| Shear bond strength, mean (MPa) | 20.53 | 18.23 | 12.45 | 14.40 | 11.38 |
| Shear bond strength, standard deviation (MPa) | 3.92 | 2.67 | 2.38 | 4.35 | 0.76 |

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims that follow.

The invention claimed is:

1. An orthodontic adhesive composition comprising:
   a hardenable component;
   a photoinitiator;
   a rigid and dimensionally stable crosslinked polymeric filler having a controlled particle size and particle size distribution,
   wherein the crosslinked polymeric filler has a particle size median in a range from 6 micrometers to 18 micrometers and a d50/d25 particle size ratio up to 1.8; and
   at least one of a silica filler and a fluoroaluminosilicate glass filler.

2. The orthodontic composition according to claim 1, wherein the crosslinked polymeric filler is an emulsion polymer.

3. The orthodontic composition according to claim 1, wherein the crosslinked polymeric filler is a suspension polymer.

4. The orthodontic composition according to claim 1, wherein the crosslinked polymeric filler has a particle size median in a range from 7 micrometers to 17 micrometers.

5. The orthodontic composition according to claim 1, wherein the crosslinked polymeric filler has a particle size median in a range from 8 micrometers to 16 micrometers.

6. The orthodontic composition according to claim 1, wherein the silica filler is present in an amount up to 5 percent based on the overall weight of the composition.

7. The orthodontic composition according to claim 1, wherein the composition includes fluoroaluminosilicate glass filler and wherein the fluoroaluminosilicate glass filler is silane treated.

8. The orthodontic composition according to claim 1, wherein the fluoroaluminosilicate glass filler is present in an amount up to 40 percent based on the overall weight of the composition.

9. The orthodontic composition according to claim 8, wherein the fluoroaluminosilicate glass filler is fluoride releasing.

10. The orthodontic composition according to claim 1, wherein the crosslinked polymeric filler is derived from at least one of: poly(methylmethacrylate), poly(styrene), or poly(styrene-ethyl methacrylate).

11. The orthodontic composition according to claim 1, wherein the crosslinked polymeric filler is present in a range from 55 percent by weight to 65 percent by weight, based on the overall weight of the composition.

12. The orthodontic composition according to claim 1, wherein the hardenable component comprises a crosslinker.

13. The orthodontic composition according to claim 1, wherein the hardenable component is present in a range from 30 to 45 percent by weight based on the overall weight of the composition.

14. The orthodontic composition according to claim 1, wherein the hardenable component comprises at least one of: a urethane dimethacrylate, bis-glycidyl methacrylate, or bis-ethyl methacrylate.

15. The orthodontic composition according to claim 1, wherein the polymeric filler is present in a range from 50 to 70 percent by weight based on the overall weight of the composition.

16. An orthodontic adhesive composition comprising:
a hardenable component;
a photoinitiator;
a rigid and dimensionally stable crosslinked polymeric filler having a controlled particle size and particle size distribution, wherein the crosslinked polymeric filler has a particle size median in a range from 6 micrometers to 18 micrometers and a d50/d25 particle size ratio up to 1.8; and
an inorganic filler, wherein the inorganic filler has a Mohs hardness of at least 5 and is present in an amount up to 5 percent by weight based on the overall weight of the composition,
wherein the composition is essentially free of any other inorganic fillers with a Mohs hardness of at least 5.

17. The orthodontic composition according to claim 16, wherein the crosslinked polymeric filler has a particle size median in a range from 8 micrometers to 16 micrometers.

18. The orthodontic composition of claim 16, wherein polymeric filler is present in a range from 50 to 70 percent by weight based on the overall weight of the composition.

19. A packaged article comprising:
an orthodontic appliance having a base for bonding the appliance to a tooth;
an adhesive on the base of the appliance, the adhesive comprising
a hardenable component;
a photoinitiator;
a rigid and dimensionally stable crosslinked polymeric filler having a controlled particle size and particle size distribution, wherein the crosslinked polymeric filler has a particle size median in a range from 6 micrometers to 18 micrometers and a d50/d25 particle size ratio up to 1.8; and
a container at least partially surrounding the orthodontic appliance having adhesive on the base thereof.

20. The article of claim 19, wherein the crosslinked polymeric filler has a particle size median in a range from 8 micrometers to 16 micrometers.

* * * * *